US008753493B2

(12) United States Patent
Lee et al.

(10) Patent No.: US 8,753,493 B2
(45) Date of Patent: Jun. 17, 2014

(54) APPARATUS FOR MEASURING BIOMATERIAL AND METHOD FOR MANUFACTURING SAME

(75) Inventors: Jin-Woo Lee, Gyeonggi-do (KR); Jae-Kyu Choi, Daejeon (KR)

(73) Assignee: Ceragem Medisys Inc., Gyeonggi-do (KR)

( * ) Notice: Subject to any disclaimer, the term of this patent is extended or adjusted under 35 U.S.C. 154(b) by 141 days.

(21) Appl. No.: 13/375,276

(22) PCT Filed: Apr. 30, 2010

(86) PCT No.: PCT/KR2010/002737
§ 371 (c)(1),
(2), (4) Date: Nov. 30, 2011

(87) PCT Pub. No.: WO2010/140772
PCT Pub. Date: Dec. 9, 2010

(65) Prior Publication Data
US 2012/0073967 A1 Mar. 29, 2012

(30) Foreign Application Priority Data
Jun. 2, 2009 (KR) .................. 10-2009-0048672

(51) Int. Cl.
*G01N 27/327* (2006.01)
(52) U.S. Cl.
CPC .................. *G01N 27/3272* (2013.01)
USPC ............. 204/403.01; 204/403.02; 204/403.14
(58) Field of Classification Search
CPC ............................................... G01N 27/3272
USPC ................ 422/68.1; 204/403.01–403.06, 409
See application file for complete search history.

(56) References Cited

U.S. PATENT DOCUMENTS

| 5,437,999 A | 8/1995 | Diebold et al. |
| 5,759,364 A | 6/1998 | Charlton et al. |

(Continued)

FOREIGN PATENT DOCUMENTS

| JP | 08-240560 A | 9/1996 |
| JP | 09-189675 A | 7/1997 |

(Continued)

OTHER PUBLICATIONS

Korean Patent Abstract of KR10-2006-0131837, published on Dec. 20, 2006, 1 page.

(Continued)

*Primary Examiner* — Luan Van
*Assistant Examiner* — Steven Rosenwald
(74) *Attorney, Agent, or Firm* — Osha Liang LLP

(57) ABSTRACT

The present invention relates to an apparatus for measuring biomaterial and a method for manufacturing thereof. The apparatus of the present invention comprises: a first substrate having a recess in one side thereof; a second substrate having a plurality of reaction electrodes where a biochemical reaction of a biomaterial occurs, and a plurality of delivery electrodes delivering signals from the reaction to a detector; and reaction reagents located in the recess causing the reaction with the biomaterial. The second substrate is attached to the first substrate such that a portion of the recess forms a sample-inlet, the recess cooperates with at least one edge of the second substrate to form at least one vent slit, and the reaction electrodes are directed toward the recess. Such apparatus of the present invention enables air in the capillary to be thoroughly and quickly discharged to the outside with biomaterial-introduction, thereby increasing the speed of the biomaterial-introduction.

14 Claims, 14 Drawing Sheets

(56) References Cited

U.S. PATENT DOCUMENTS

| | | | |
|---|---|---|---|
| 6,071,391 A * | 6/2000 | Gotoh et al. | 204/403.05 |
| 6,117,292 A * | 9/2000 | Ahmad | 204/416 |
| 6,153,070 A * | 11/2000 | Maurer et al. | 204/416 |
| 7,070,680 B2 * | 7/2006 | Bae et al. | 204/403.04 |
| 7,138,041 B2 * | 11/2006 | Su et al. | 204/403.04 |
| 2008/0087075 A1 * | 4/2008 | Creaven et al. | 73/61.41 |
| 2011/0100812 A1 * | 5/2011 | Takenaka et al. | 204/412 |

FOREIGN PATENT DOCUMENTS

| | | |
|---|---|---|
| KR | 10-2006-0131837 A | 12/2006 |
| KR | 100890988 B1 | 3/2009 |
| WO | 03/048756 A1 | 6/2003 |

OTHER PUBLICATIONS

Korean Patent Abstract of Registration No. 100890988 B1, issued Mar. 23, 2009, 1 page.

International Search Report issued in PCT/KR2010/002737, mailed Dec. 3, 2010, with translation, 5 pages.

Written Opinion issued in PCT/KR2010/002737, mailed Dec. 3, 2010, 3 pages.

* cited by examiner

APPARATUS FOR MEASURING BIOMATERIAL AND METHOD FOR MANUFACTURING SAME

TECHNICAL FIELD

The present invention relates to an apparatus for measuring a biomaterial and a method of manufacturing the same, and more particularly, to a biosensor for selectively performing quantitative analysis on specific materials in bio-samples such as blood and a method of manufacturing the same.

BACKGROUND ART

Biosensors are measuring instruments that examine the properties of a substance using functions of an organism. These biosensors are excellent in sensitivity and reaction specificity because the biosensors use a biomaterial as detecting element. Thus, the biosensors are broadly used in various fields such as clinical chemical analysis, process instrumentation of bioindustry, environment instrumentation, stability evaluation of chemicals, and so on, and their usage is continuing to spread. Particularly, a variety of biosensors are used in a medical diagnostic field to analyze samples, particularly bio-samples. The biosensors are divided into enzyme assay biosensors and immunoassay biosensors according to the kind of detecting element, and into optical biosensors and electrochemical biosensors according to a method of quantitatively analyzing a target substance within a bio-sample.

The enzyme assay biosensors are designed to use a specific reaction between an enzyme and a substrate and a specific reaction between an enzyme and an enzyme inhibitor, and the immunoassay biosensors are designed to use a specific reaction between an antigen and an antibody.

The optical biosensors are widely used to measure a concentration of a target material by measuring transmittance, absorbance, or alteration in wavelength. The optical biosensors have an advantage in that, since reaction mechanisms of various materials to be analyzed have already been known and measurement is made after a reaction takes place for a sufficient time, a deviation in measurement time is low. In contrast, the optical biosensors have a disadvantage in that they require a longer measurement time and a greater quantity of samples than the electrochemical biosensors. Further, the optical biosensors have other disadvantages in that measured results are influenced by turbidity of a sample, and it is difficult to miniaturize an optical unit.

The electrochemical biosensors are used to measure a concentration of a target material by measuring an electric signal obtained from a reaction. The electrochemical biosensors have advantages in that it is possible to amplify a signal using a very small quantity of sample, they are easy to miniaturize, it is possible to stably obtain a measured signal, and they can be easily combined with a telecommunication instrument. However, the electrochemical biosensors have disadvantages in that an electrode manufacturing process is additionally required, the cost of production is high, and a measured signal is very sensitive to response time.

Meanwhile, a capillary structure is typically used to introduce a biomaterial such as a sample into a measuring region of the biosensor. In the case of conventional biosensors using such a capillary structure, a vent hole is generally formed in some of substrates forming a capillary. This vent hole allows air in the capillary to be discharged to the outside while a bio-sample is introduced into the capillary of the biosensor, thereby forcing the bio-sample to be continuously introduced into the capillary.

A biosensor having an opposing electrode structure is disclosed in U.S. Pat. No. 5,437,999. In this biosensor, three substrates including spacer are adhered to form a capillary gap, and upper and lower substrates are each provided with a vent hole at the same position. Thus, when a sample is introduced into the capillary gap defined by the three substrates including the spacer, air in the capillary gap is discharged to the outside via the vent holes formed in the upper and lower substrates. Another biosensor is disclosed in U.S. Pat. No. 5,759,364, in which several substrates including an embossed substrate are adhered to form a capillary gap. In the biosensor, the uppermost substrate is provided with a vent hole to discharge air in the capillary gap when a sample is introduced.

In the case of these conventional biosensors, the capillary gap is formed by deforming or processing the substrate, so that the manufacturing process is complicated and expensive. Further, when the sample is introduced into the capillary gap, the air in the capillary gap is pushed out only through the vent hole, and thus the sample is introduced at a low speed. In addition, when a capillary wall has high friction, the sample may be introduced at a lower speed.

DISCLOSURE

Technical Problem

An objective of the present invention is to provide a biosensor in which a sample is introduced into a capillary gap (or a reaction chamber) at a high speed.

Another objective of the present invention is to provide a biosensor in which a capillary gap (or a reaction chamber) for introducing a sample is formed by a very simple manufacturing process.

Still another objective of the present invention is directed to introducing a sample at a high speed by causing air in a reaction chamber to be discharged toward the outside at a sufficiently high speed when the sample is introduced into the reaction chamber.

Yet another objective of the present invention is directed to preventing an introducing speed of a sample from being reduced by friction against a capillary wall.

The objectives of the present invention are not limited to those mentioned above. Other objectives and advantages of the present invention which are not disclosed will be understood from the following description, and be apparent with reference to the embodiments of the present invention. Also, it is obvious to those skilled in the art that the objectives and advantages of the present invention will be realized by the means as claimed and combinations thereof.

Technical Solution

In order to achieve the above objectives, according to one aspect of the present invention, there is provided an apparatus for measuring a biomaterial, which includes: a first substrate having a recess formed in one side surface thereof; a second substrate having a plurality of reaction electrodes in which a biochemical reaction of a sample occurs and a plurality of delivery electrodes transmitting a signal generated by the biochemical reaction to a detector; and an reaction reagent located in the recess and causing the biochemical reaction with the sample, wherein the second substrate is attached to the first substrate such that the reaction electrodes are directed toward the recess and the recess forms at least one vent slit in combination with at least one edge surface of the second substrate, and the first and second substrate are attached to form a sample inlet and a reaction chamber.

According to another aspect of the present invention, there is provided an apparatus for measuring a biomaterial, which includes: a first substrate having a recess formed in one side surface thereof a second substrate; a plurality of electrodes attached to the first or second substrate; and an reaction reagent located in the recess and causing the biochemical reaction with a sample, wherein the second substrate is attached to the first substrate such that the recess forms at least one vent slit in combination with at least one edge surface of the second substrate.

According to yet another aspect of the present invention, there is provided a method of manufacturing an apparatus for measuring a biomaterial, which includes: manufacturing a first substrate having a recess formed in one surface thereof; manufacturing a second substrate having a plurality of reaction electrodes in which a biochemical reaction of a sample occurs and a plurality of delivery electrodes transmitting a signal generated by the biochemical reaction to a detector; immobilizing a reaction reagent causing the biochemical reaction with the sample to the first or second substrate so as to be located in the recess; and attaching the second substrate to the first substrate such that the reaction electrodes are directed toward the recess, and the recess forms at least one vent slit in combination with at least one edge surface of the second substrate, thereby forming a sample inlet and a reaction chamber.

Advantageous Effects

According to the present invention, a capillary gap (or a reaction chamber) for introducing a sample can be formed using a very simple manufacturing process.

Further, when the sample is introduced into the reaction chamber, air in the reaction chamber is allowed to be discharged toward the outside at a sufficiently high speed, so that it is possible to introduce the sample at a high speed. In addition, it is possible to prevent the introduction speed of the sample from being reduced by friction against a capillary wall.

BEST MODE

Mode for Invention

The foregoing and other objects, features and advantages of the invention will become more apparent from the following detailed description when read in conjunction with the accompanying drawings. Accordingly, it will be easily understood by those skilled in the art that the invention can be modified in various forms without departing from the technical spirit of the invention. In the following description, well-known functions or constructions are not described in detail since they would obscure the invention in unnecessary detail. Exemplary embodiments of the invention will be described below in detail with reference to the accompanying drawings.

Figure 1:
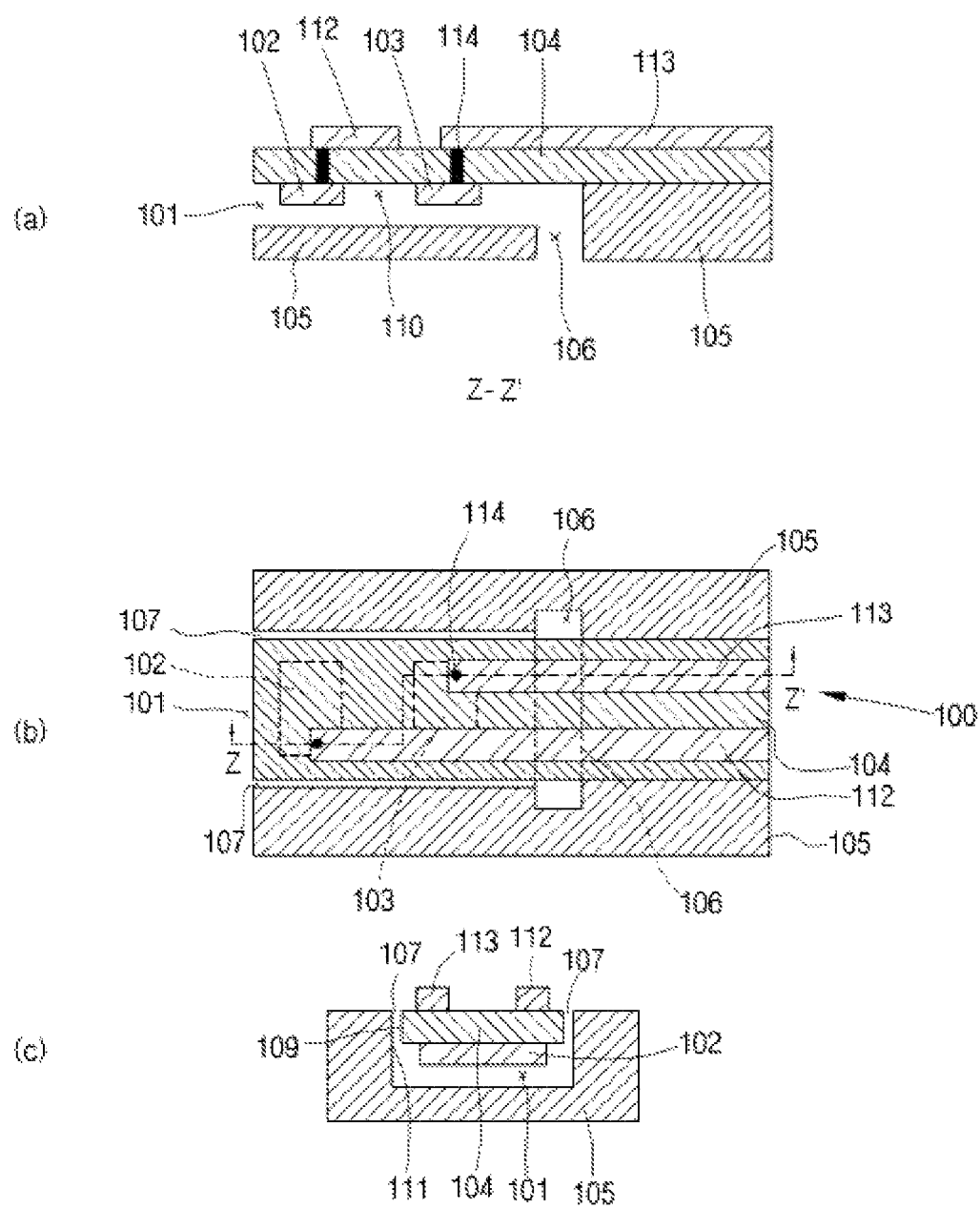
FIG. 1 is a view for explaining the structure of a biosensor according to a first embodiment of the present invention.

FIG. 1 is a view for explaining the structure of a biosensor according to a first embodiment of the present invention. Particularly, FIG. 1(a) is a cross-sectional view of the biosensor, FIG. 1(b) is a plan view of the biosensor, and FIG. 1(c) is a front view of the biosensor.

Referring to FIG. 1, the biosensor according to the first embodiment of the present invention includes a first substrate having a recess and a sample inlet, and a second substrate having a plurality of reaction electrodes and a plurality of delivery electrodes.

The first substrate 105 is a attachbasement substrate that serves as a physical support, and is provided with a recess 110 in one side surface thereof. A portion, preferably one end, of the recess 110 forms a sample inlet The second substrate 104 is a reaction substrate having a reference electrode 102, a working electrode 103, a first delivery electrode 112, and a second delivery electrode 113. A reaction reagent (not shown) is immobilized to the second substrate 104 across the reference electrode 102 and the working electrode 103, so that it is located in the recess 110. A biochemical reaction between the reaction reagent and the sample takes place around the reference and working electrodes 102 and 103, on which the reaction reagent is immobilized. The first delivery electrode 112 is electrically connected to the reference electrode 102, whereas the second delivery electrode 113 is electrically connected to the working electrode 103. Thereby, an electric signal generated from the reference electrodes 102 and working electrodes 103 by the biochemical reaction between the reaction reagent and the sample is transmitted to a detector. Herein, the electrodes, such as the reference electrode and the working electrode, which relate to the biochemical reaction are generically referred to as "reaction electrodes," which are distinguished from the delivery electrodes that transmit the electric signal generated by the biochemical reaction to a measuring apparatus. The reference electrode is generally called a "counter electrode" in the related art.

Referring to FIGS. 1(a) to 1(c), the first substrate 105 having the recess 110 whose front side is opened and the second substrate 104 having electrodes and a planar structure are attached to each other, so that the front side of the recess is formed as the sample inlet 101. Alternatively, in the first substrate, only a portion of the recess whose front side is closed may be covered by the second substrate, and the other parts of the recess may be opened toward the top surface of the first substrate to form the sample inlet.

When the first and second substrates 105 and 104 are attached to each other, a reaction chamber is formed in a capillary structure. That is, the first substrate 105 is covered by the second substrate 104, so that the recess 110 formed in the first substrate is formed as a path for the biomaterial introduction or a reaction chamber having a capillary structure. The second substrate 104 is attached to the first substrate 105 such that the reference electrode 102 and the working electrode 103 are directed toward the recess 110 and that a vent slit 107 is formed by a combination of the recess 110 and at least one edge surface 109 of the second substrate 104. The vent slit 107 continuously extends from the sample inlet 101 in a lengthwise direction of the biosensor 100. Herein, the lengthwise direction of the biosensor 100 refers to a direction in which the sample is introduced into the recess 110 or the reaction chamber. The lengthwise direction of the biosensor 100 is equivalent to a lengthwise direction of the sample inlet 101, so that the two directions are interchangeable with each other herein.

The reference electrode 102 and the working electrode 103 are formed on a surface of the second substrate 104 which is directed toward the recess 110, whereas the first and second delivery electrodes 112 and 113 are formed on the opposite surface of the second substrate 104. The first and second delivery electrodes 112 and 113 are electrically connected to the reference electrode 102 and the working electrode 103 via conductors 114 passing through the second substrate 104, respectively.

In this embodiment, the first and second delivery electrodes 112 and 113 and the reference electrode 102 and the working electrode 103 are formed on the respective different surfaces of the second substrate 104, but they may be formed on the same surface of the second substrate 104. Further, in this embodiment, in the recess 110 formed in the first substrate 105, a vent hole 106 is formed in the other end of the front side of the recess on which the sample inlet 101 is formed. Alternatively, the vent hole 106 may be formed in the second substrate 104 rather than the first substrate 105, or may not be formed in any substrate.

The sample is introduced into the reaction chamber by a capillary phenomenon. The capillary phenomenon occurs between a surface of the second substrate 104 which is directed toward the recess 110 and a bottom surface of the recess 110 of the first substrate 105 as well as between the edge surface 109 of the second substrate 104 and a wall 111 of the recess 110. In detail, the one or more vent slits 107 formed between the edge surface 109 of the second substrate to 104 and the wall 111 of the recess 110 serve as an air outlet when the sample is introduced. Thus, the vent slit 107 discharges air in the reaction chamber toward the outside and simultaneously introduces the sample into the reaction chamber by means of the capillary phenomenon, thereby making it faster to introduce the sample into the reaction chamber.

The second substrate 104 is physically isolated within a gap where the sample reacts with the reaction reagent. That is, unlike existing biosensors, the second substrate 104 is not in contact with the other substrate due to the vent slit 107 within the gap. In this embodiment, the vent slit 107 is not formed by separately processing a specific substrate, but it is three-dimensionally formed as a result of adjusting a positional relationship between the second substrate 104 and the first substrate 105. A gap of the vent slit 107 can be easily adjusted by a thickness of the second substrate 104.

Figure 2:
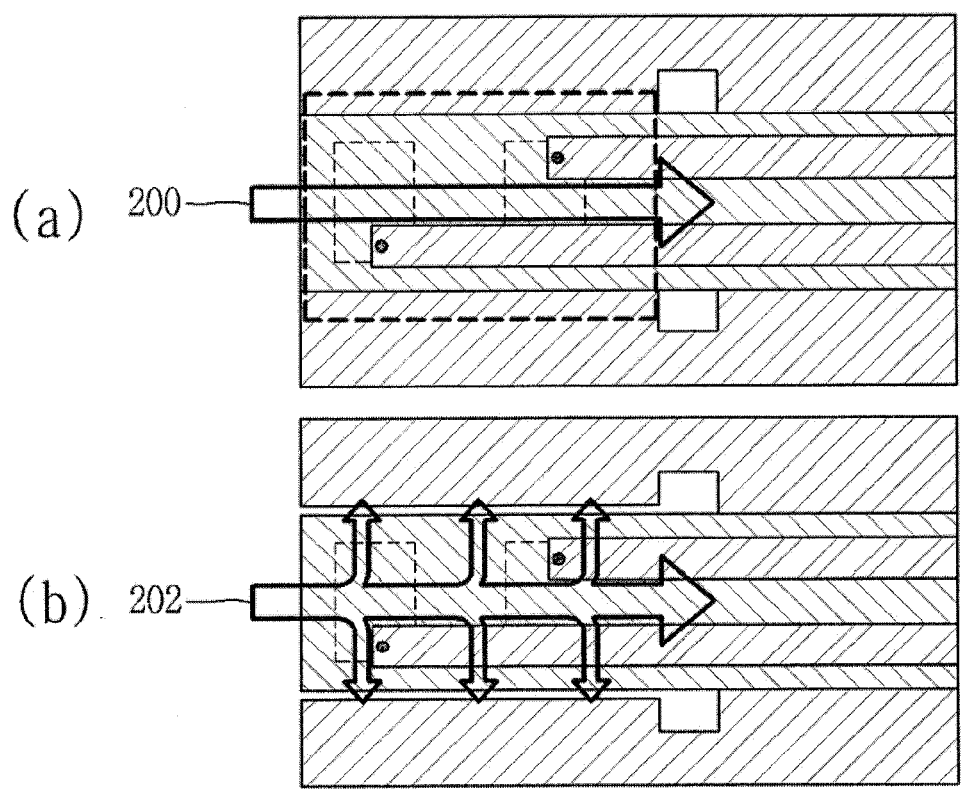
FIG. 2 is a view for explaining how air is discharged from a capillary of the biosensor shown in FIG. 1.

FIG. 2 is a view for explaining how air is discharged from the reaction chamber of the biosensor shown in FIG. 1. FIG. 2(a) shows only the vent hole 106 being formed in the first substrate 105, and FIG. 2(b) shows both the vent hole 106 and the vent slits 107 being formed. In FIG. 2(a), as a sample is introduced into the reaction chamber having a capillary structure, air 200 in the reaction chamber is discharged to the outside only via the vent hole 106. As such, the sample is introduced at a low speed. In contrast, in FIG. 2(b), the air 200 in the reaction chamber is discharged to the outside via both the vent hole 106 and the vent slits 107. As such, the sample is introduced at a higher speed.

Further, since a width of the vent slit 107 is smaller than an interval between the surface of the second substrate 104 which is directed toward the recess 110 and the bottom surface of the recess 110, this structure of the biosensor 100 causes a stronger capillary phenomenon. Thus, the introduction of the sample into the reaction chamber becomes faster due to the capillary phenomenon caused by the vent slits 107.

Figure 3:
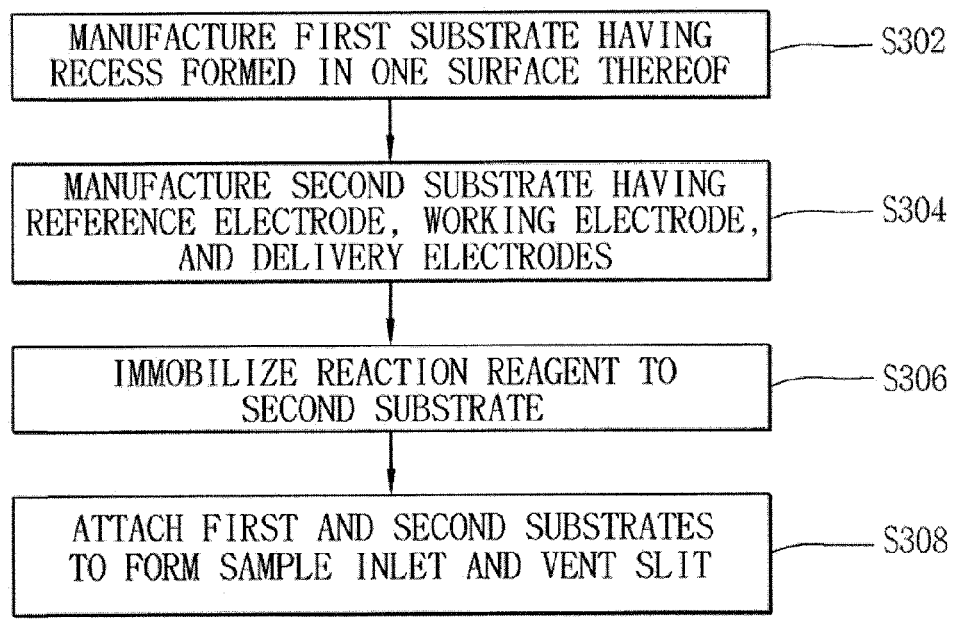
FIG. 3 is a flow chart for explaining a method of manufacturing the biosensor according to the first embodiment of the present invention.

FIG. 3 is a flow chart for explaining a method of manufacturing the biosensor according to to the first embodiment of the present invention. First, the first substrate 105 having the recess 110 in one side surface thereof is manufactured (S302). The first substrate 105 may be manufactured using injection molding, extrusion molding, or plastic laminating. Next, the second substrate 104, which has the reference and working electrodes 102 and 103 that participate in a biochemical reaction and the first and second delivery electrodes 112 and 113 that transmit an electric signal generated by the biochemical reaction to a detector, is manufactured (S304). Alternatively, step S304 of manufacturing the second substrate 104 may be followed by step S302 of manufacturing the basement substrate.

Next, a reaction reagent (not shown) causing the biochemical reaction with a sample is immobilized across the reference electrode 102 and the working electrode 103 (S306). Subsequently, the second substrate 104 is attached to the first substrate 105 such that the sample inlet 101 and the reaction chamber are formed, at least one vent slit 107 is formed in a lengthwise direction of the biosensor 100 by a combination of the recess 110 and at least one edge surface 109 of the second substrate 104, and the reference electrode 102 and the working electrode 103 are directed toward the recess 110 (S308).

In conventional biosensors, it is necessary to deform and process a specific substrate in order to form a capillary gap, and then to attach a plurality of substrates. In this embodiment, the second substrate need only be attached to the first substrate manufactured by, for instance, injection molding, and thus the manufacturing process is very simple. In detail, in the conventional biosensors, at least three substrates are required to form the capillary gap or the reaction chamber. In this invention, the reaction chamber and the vent slits, both of which have a capillary structure, can be formed by attaching only the two substrates (the first and second substrates), and thus the manufacturing process is simplified.

Figure 4:
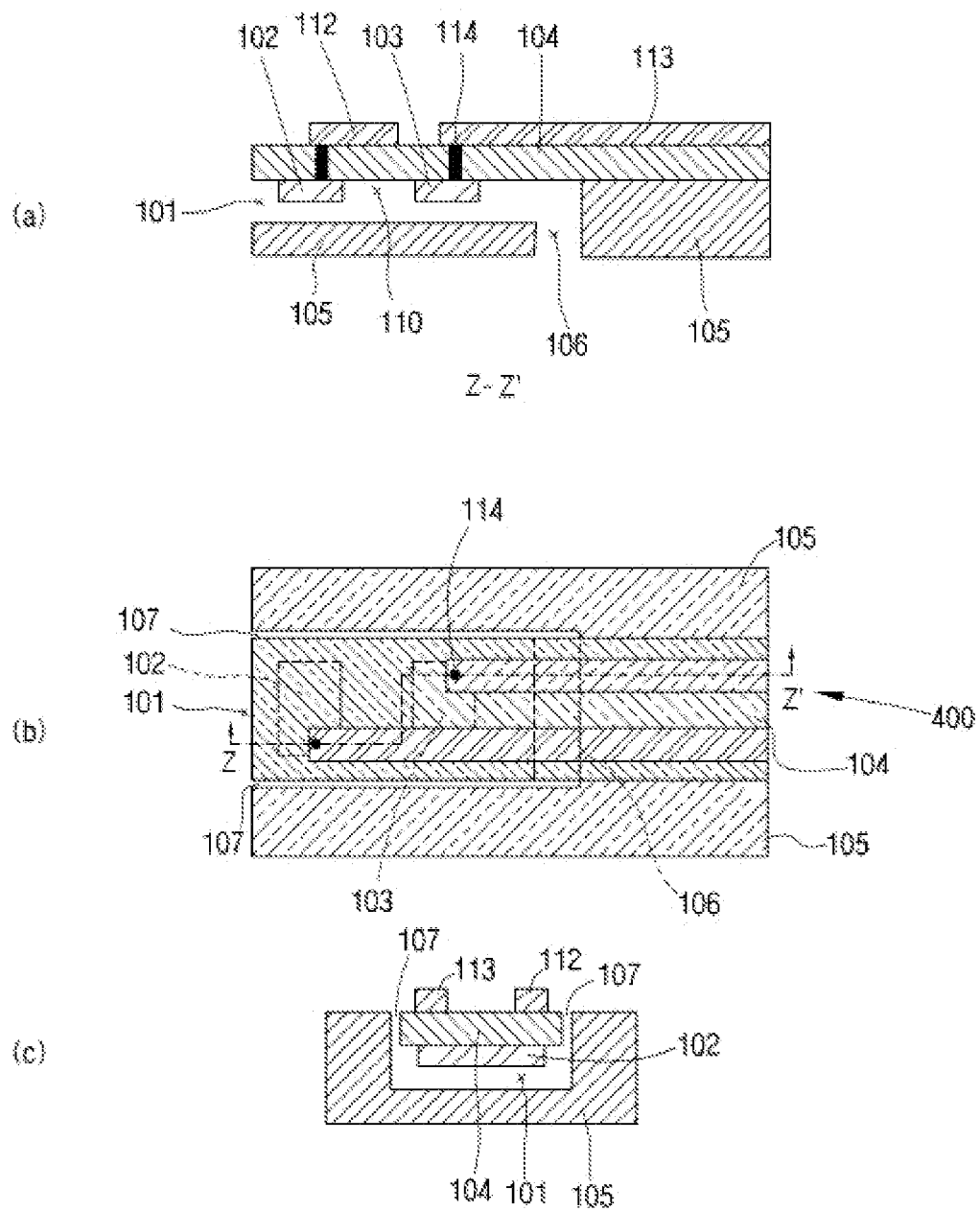
FIG. 4 is a view for explaining the structure of a biosensor according to a second embodiment of the present invention.

FIG. 4 is a view for explaining the structure of a biosensor according to a second embodiment of the present invention. FIG. 4(a) is a cross-sectional view of the biosensor, FIG. 4(b) is a plan view of the biosensor, and FIG. 4(c) is a front view of the biosensor.

Figure 5:
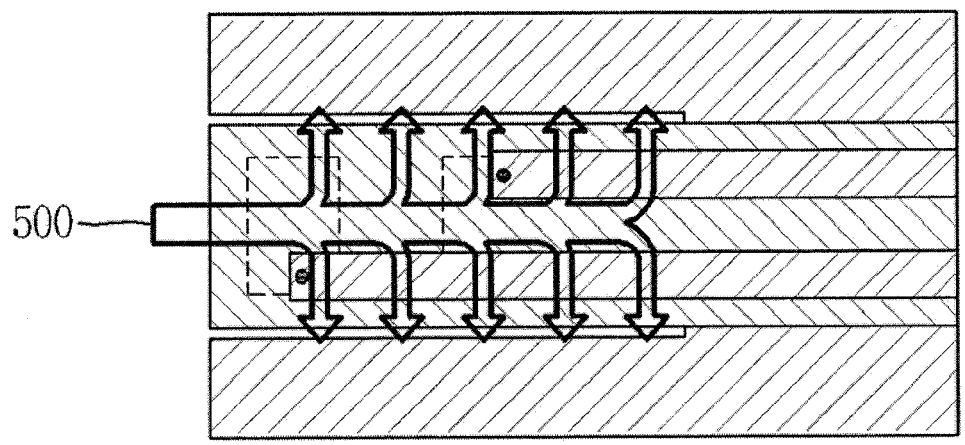
FIG. 5 is a view for explaining how air is discharged from a capillary of the biosensor shown in FIG. 4.

In comparison with the biosensor 100 of the first embodiment shown in FIG. 1, a biosensor 400 of the second embodiment shown in FIG. 4 is different in that it has no vent hole. However, all the other components are the same. As described above with reference to FIG. 2, the vent slits 107 serve as an air outlet that discharges air in the reaction chamber toward the outside when the sample is introduced into the reaction chamber. As such, even when the biosensor 400 does not have a separate vent hole, the sample can be rapidly introduced into the reaction chamber. FIG. 5 shows how air 500 in the reaction chamber is discharged via the vent slits 107 in the biosensor 400 shown in FIG. 4. However, if a width of the vent slit 107 is too small to sufficiently serve as the air outlet, a speed at which the sample is introduced into the reaction chamber may be somewhat reduced.

Figure 6:
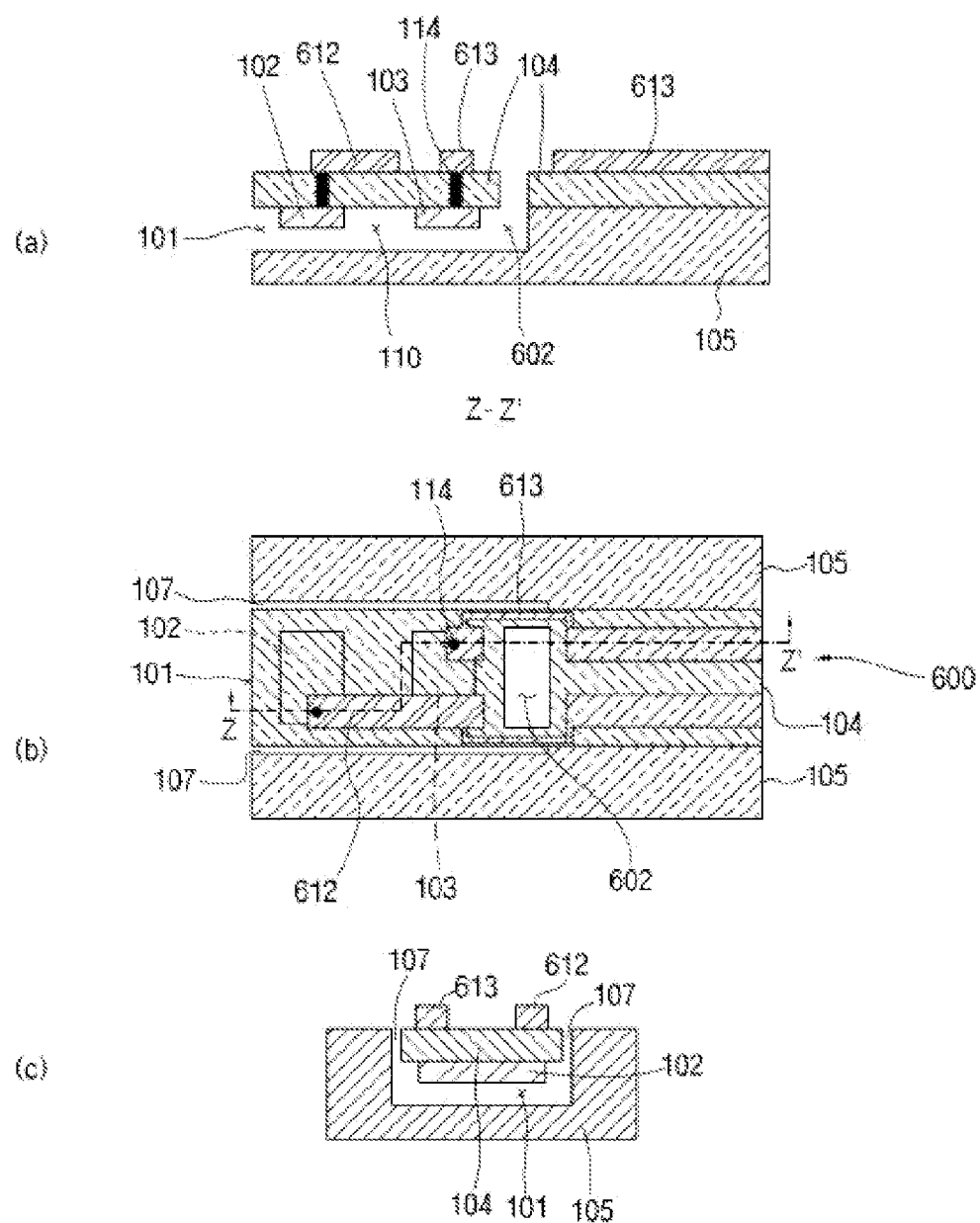
FIG. 6 is a view for explaining the structure of a biosensor according to a third embodiment of the present invention.

FIG. 6 is a view for explaining the structure of a biosensor 600 according to a third embodiment of the present invention. FIG. 6(*a*) is a cross-sectional view of the biosensor, FIG. 6(*b*) is a plan view of the biosensor, and FIG. 6(*c*) is a front view of the biosensor.

Figure 7:
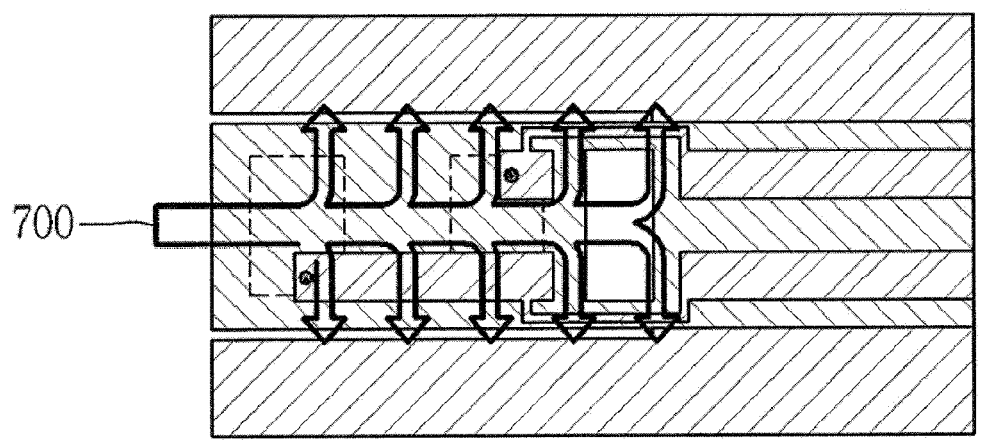
FIG. 7 is a view for explaining how air is discharged from a capillary of the biosensor shown in FIG. 6.

The biosensor 100 shown in FIG. 1 has the vent hole 106 formed in the first substrate 105, whereas the biosensor 600 shown in FIG. 6 has a vent hole 602 formed in the second substrate 104. In this respect, they are different from each other. However, all the other components are the same. FIG. 7 shows how air 700 in the reaction chamber is discharged via the vent slits 107 and the vent hole 602 in the biosensor 600 shown in FIG. 6.

Referring to FIG. 6, the first substrate 105 is a basement substrate that serves as a physical support, and has a recess formed in one side surface thereof. A portion, preferably one end, of the recess 110 forms a sample inlet 101. The second substrate 104 is a reaction substrate having a reference electrode 102, a working electrode 103, and delivery electrodes 612 and 613. Since the vent hole 602 is formed in the second substrate 104, the delivery electrodes 612 and 613 are formed around the vent hole 602. A reaction reagent (not shown) is immobilized to the second substrate 104 across the reference electrode 102 and the working electrode 103, so that it is located in the recess 110. A biochemical reaction between the reaction reagent and the sample takes place around the reference and working electrodes 102 and 103, to which the reaction reagent is immobilized. The first delivery electrode 112 is electrically connected to the reference electrode 102, and the second delivery electrode 113 is electrically connected to the working electrode 103. Thereby, an electric signal generated from the reference and working electrodes 102 and 103 by the biochemical reaction between the reaction reagent and the sample is transmitted to a detector.

When the first and second substrates 105 and 104 are attached to each other, a reaction chamber is formed in a capillary structure. The second substrate 104 is attached to the first substrate 105 such that the reference electrode 102 and the working electrode 103 are directed toward the recess 110 and that the recess 110 forms a vent slit 107 in combination with at least one edge surface 109 of the second substrate 104. The vent slit 107 continuously extends from the sample inlet 101 in a lengthwise direction of the sample inlet 101.

The reference electrode 102 and the working electrode 103 are formed on a surface of the second substrate 104 which is directed toward the recess 110, and the first and second delivery electrodes 612 and 613 electrically connected to the reference electrode 102 and the working electrode 103, respectively, are formed on the opposite surface of the second substrate 104. The first and second delivery electrodes 612 and 613 are electrically connected to the reference electrode 102 and the working electrode 103 via conductors 114 or conductive clamping members (not shown) passing through the second substrate 104, respectively.

Hereinafter, a method of manufacturing the biosensor shown in FIG. 6 will be described. First, the first substrate 105 having the recess formed in one side surface thereof is manufactured. The first substrate 105 may be manufactured using injection molding, extrusion molding, or plastic laminating. Next, the second substrate 104 is manufactured, which has the reference and working electrodes 102 and 103 that participate in a biochemical reaction, the first and second delivery electrodes 612 and 613 that transmit an electric signal generated by the biochemical reaction to a detector, and the vent hole 602 (S304). When manufacturing the second substrate 104, the reference electrode 102, the working electrode 103, and the delivery electrodes 612 and 613 may be formed using semiconductor process technology, and then the vent hole 602 may be formed.

Next, a reaction reagent (not shown) causing a biochemical reaction with a sample is immobilized across the reference electrode 102 and the working electrode 103. Subsequently, the second substrate 104 is attached to the first substrate 105 such that the sample inlet 101 and the reaction chamber are formed, at least one vent slit 107 is formed in a lengthwise direction of the biosensor 100 by a combination of the recess and an edge surface of the second substrate, and the reference electrode 102 and the working electrode 103 are directed toward the recess of the first substrate 105.

Figure 8:
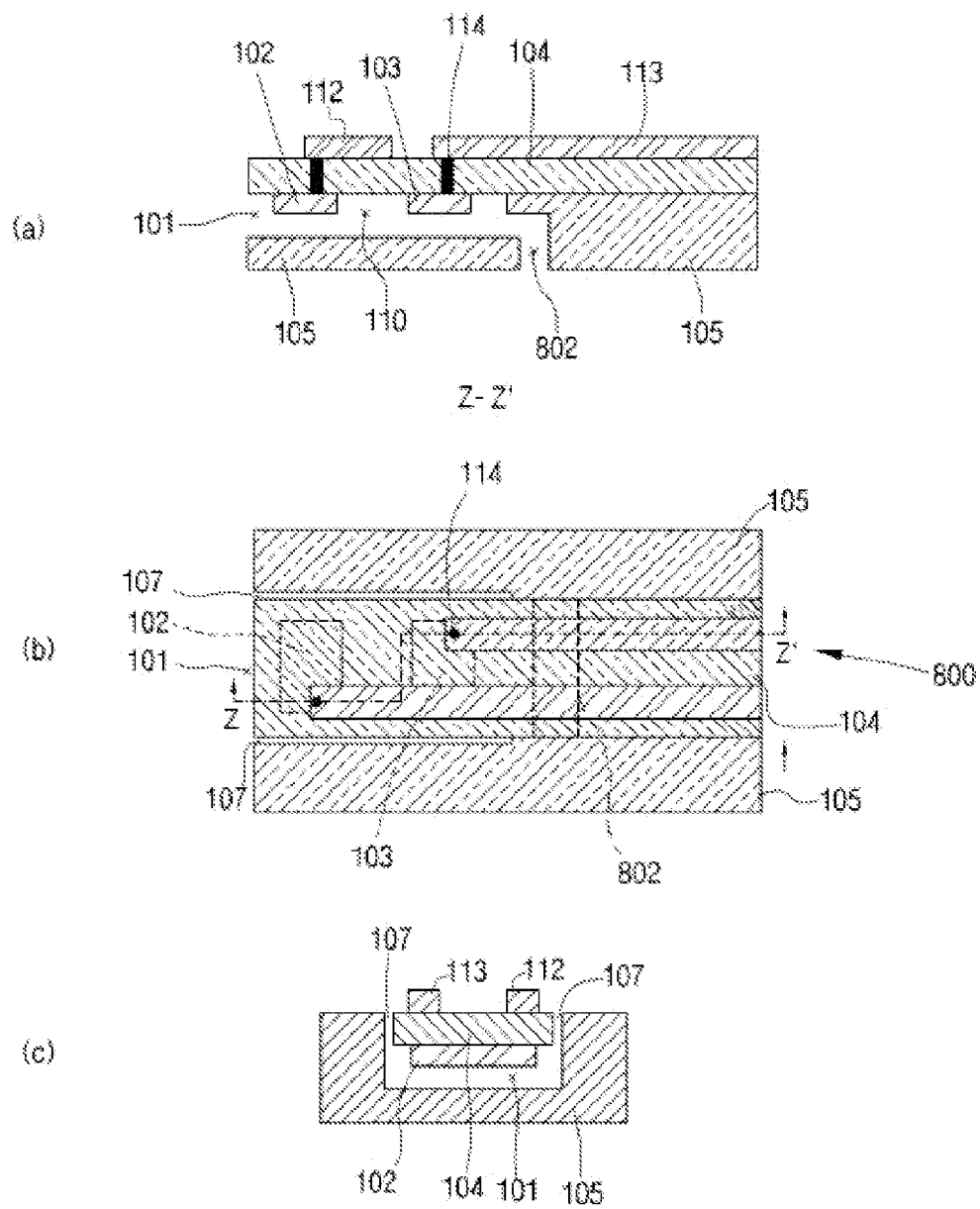
FIG. 8 is a view for explaining the structure of a biosensor according to a fourth embodiment of the present invention.

FIG. 8 is a view for explaining the structure of a biosensor according to a fourth embodiment of the present invention. FIG. 8(*a*) is a cross-sectional view of the biosensor, FIG. 8(*b*) is a plan view of the biosensor, and FIG. 8(*c*) is a front view of the biosensor. The biosensor 100 shown in FIG. 1 has the vent hole 106 formed within the reaction chamber, whereas the biosensor 800 shown in FIG. 8 has a vent hole 802 formed beyond the reaction chamber. In this respect, they are different from each other.

Figure 9:
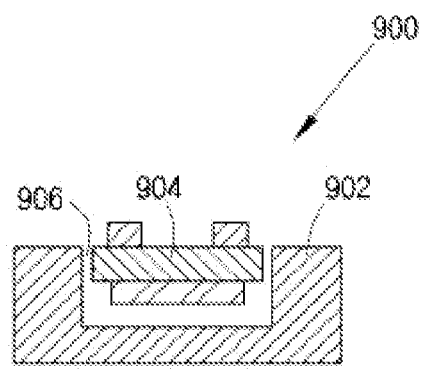
FIG. 9 is a front view of a biosensor according to a fifth embodiment of the present invention.

FIG. 9 is a front view of a biosensor according to a fifth embodiment of the present invention. The biosensor 100 shown in FIG. 1 is configured so that the top surface of the second substrate 104 is flush with the top surface of the first substrate 105, whereas the biosensor 900 shown in FIG. 9 is configured so that the top surface of a second substrate 904 is different in height from the top surface of a first substrate 905. That is, the top surface of the second substrate 904 is slightly raised over the top surface of a first substrate 905.

Figure 10:
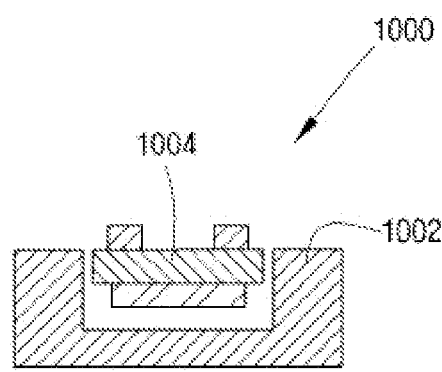
FIG. 10 is a front view of a biosensor according to a sixth embodiment of the present invention.

FIG. 10 is a front view of a biosensor according to a sixth embodiment of the present invention. The biosensor 100 shown in FIG. 1 is configured so that the vent slits having the same width are formed along the opposite edges of the second substrate 104, whereas a biosensor 1000 shown in FIG. 10 is configured so that a vent slit is only formed along the edge of a second substrate 1004. That is, the second substrate 1004 is unbalanced to one side of a first substrate 1005.

Figure 11:
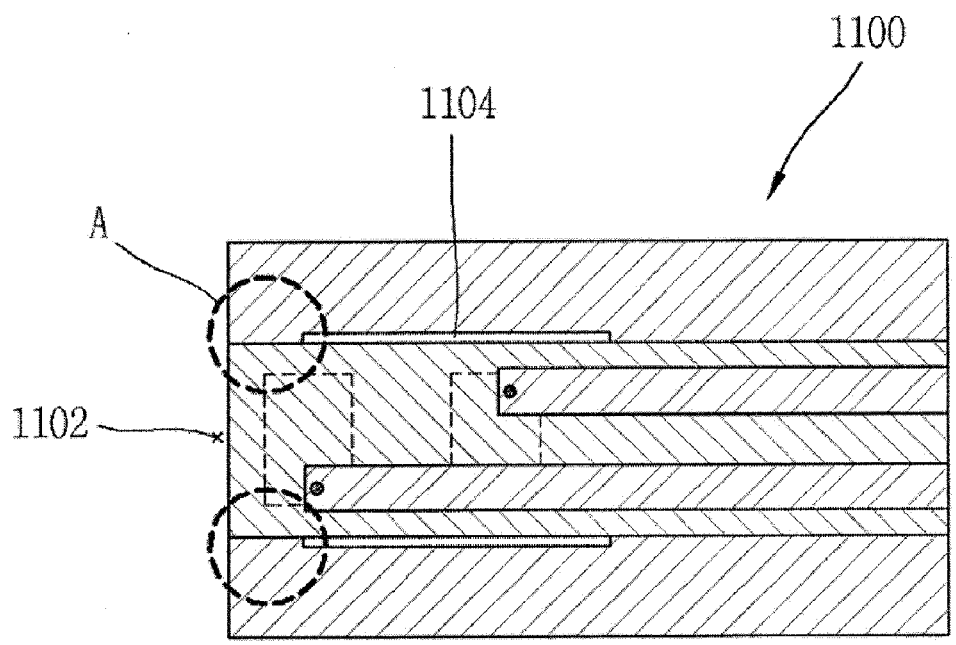
FIG. 11 is a plan view of a biosensor according to a seventh embodiment of the present invention.

FIG. 11 is a plan view of a biosensor according to a seventh embodiment of the present invention. A biosensor 1100 is characterized in that vent slits 1104 discontinuously extend from a sample inlet 1102 as indicated by "A."

Figure 12:
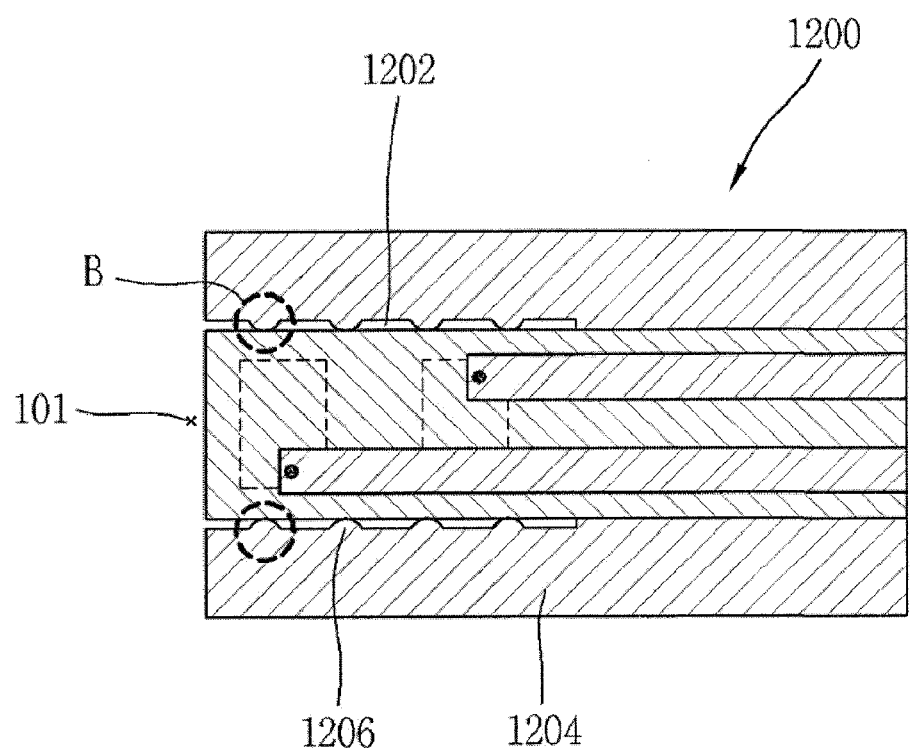
FIG. 12 is a plan view of a biosensor according to an eighth embodiment of the present invention.

FIG. 12 is a plan view of a biosensor according to an eighth embodiment of the present invention. A biosensor 1200 is characterized in that at least one protrusion 1206 protrudes from a first substrate 1204 at an intermediate portion of each vent slit 1202 as indicated by "B."

Figure 13:
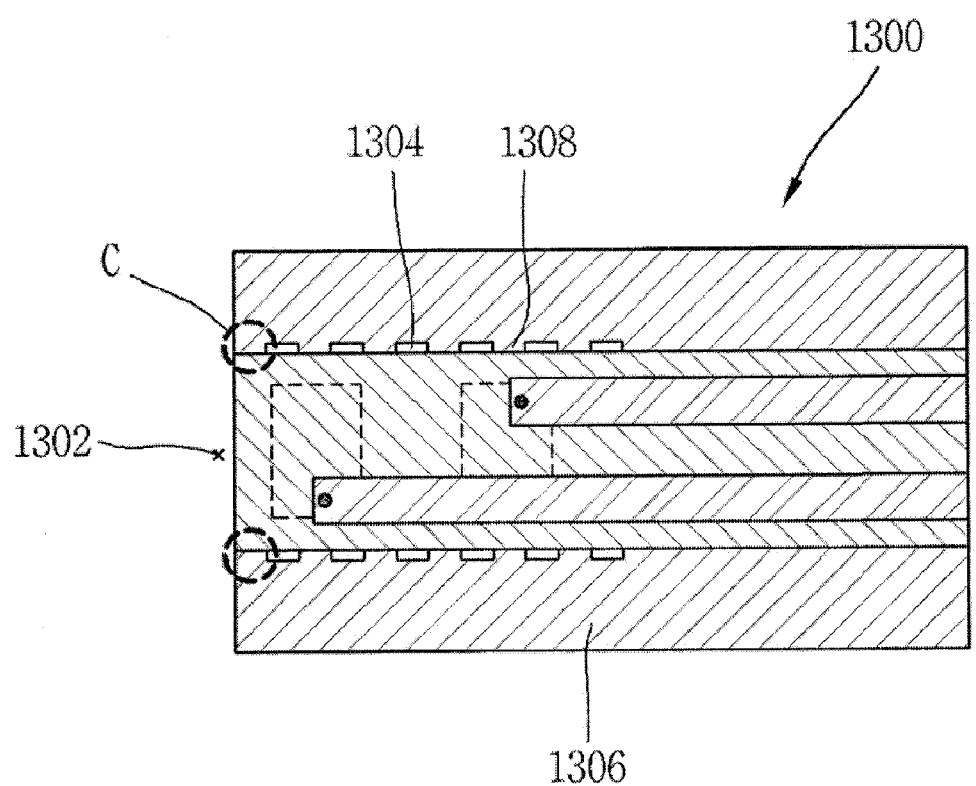
FIG. 13 is a plan view of a biosensor according to a ninth embodiment of the present invention.

FIG. 13 is a plan view of a biosensor according to a ninth embodiment of the present invention. A biosensor 1300 is characterized in that at least one protrusion 1308 protrudes from a first substrate 1306 at an intermediate portion of each vent slit 1304, and each vent slit 1304 discontinuously extends from a sample inlet 1302 due to the protrusion 1308, as indicated by "C."

Figure 14:
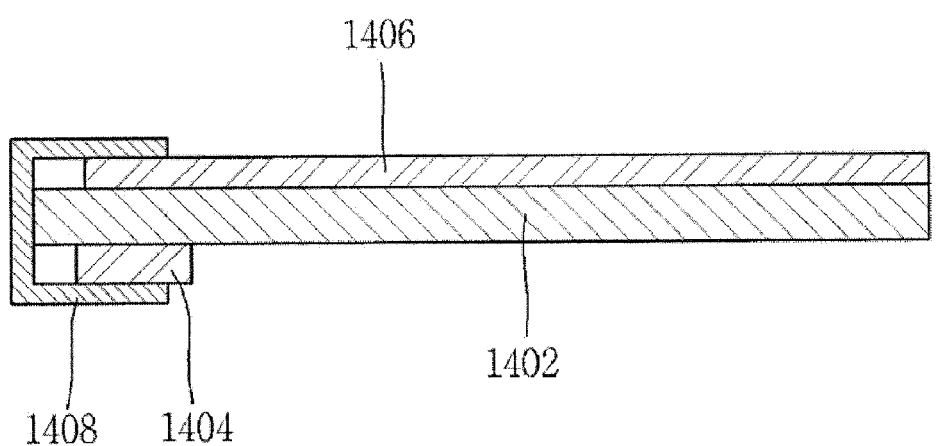
FIG. 14 is a view for explaining another embodiment where reaction electrodes and delivery electrodes of the present invention are electrically connected to each other.

FIG. 14 is a view for explaining another embodiment where reaction electrodes and delivery electrodes of the present invention are electrically connected to each other. As shown, a first or second delivery electrode 1406 formed on one side of a second substrate 1402 may be electrically connected to a reaction electrode 1404 via a conductive clamping member 1408 formed on an edge of the second substrate 1402. To stably fix the delivery electrode 1406 and the reaction electrode 1404, the conductive clamping member 1408 may be formed of a resilient material.

Although specific embodiments of the invention have been described with reference to the drawings, the invention is not limited to these specific embodiments. It is apparent to those skilled in the art that various modifications, additions and substitutions are possible without departing from the scope of the present invention which is intended to be defined by the appended claims. Particularly, the above embodiments are based on a two-electrode system. However, it will be understood that the present invention may be applied to all types of electrode systems including a three-electrode system.

The invention claimed is:

1. An apparatus for measuring a biomaterial, comprising:
    a first substrate having a recess formed in an upper surface thereof;
    a second substrate having a plurality of reaction electrodes in which a biochemical reaction of a sample occurs and a plurality of delivery electrodes transmitting a signal generated by the biochemical reaction to a detector; and
    a reaction reagent located in the recess and causing the biochemical reaction with the sample,
    wherein the second substrate is located in the recess and attached to the first substrate such that a reaction chamber is formed between a lower surface of the second substrate and a bottom surface of the recess, the reaction electrodes are directed toward the bottom surface of the recess in the reaction chamber, and a vent slit is formed between a side wall of the recess and a side edge surface of the second substrate, and
    the first and second substrates are attached to form a sample inlet.

2. The apparatus according to claim 1, wherein the vent slit continuously extends from the sample inlet.

3. The apparatus according to claim 1, wherein the vent slit is formed in a lengthwise direction of the sample inlet.

4. The apparatus according to claim 1, wherein the reaction electrodes and the delivery electrodes are folined on the lower surface one and an upper surface of the second substrate, respectively; and
    the reaction electrodes and the delivery electrodes are electrically connected to each other.

5. The apparatus according to claim 4, wherein the delivery electrodes are electrically connected to the reaction electrodes via conductors passing through the second substrate.

6. The apparatus according to claim 4, wherein the delivery electrodes are electrically connected to the reaction electrodes via conductive clamping members.

7. The apparatus according to claim 1, wherein the reaction electrodes and the delivery electrodes are formed on the same surface of the second substrate.

8. The apparatus according to claim 1, further comprising a vent hole formed in the first or second substrate on an opposite side of the sample inlet.

9. The apparatus according to claim 1, wherein the reaction reagent is immobilized to the reaction electrodes.

10. The apparatus according to claim 1, wherein the width of the second substrate is smaller than the width of the recess.

11. An apparatus for measuring a biomaterial, comprising:
    a first substrate having a recess formed in an upper surface thereof;
    a second substrate located in the recess and attached to the first substrate to form a reaction chamber between a lower surface of the second substrate and a bottom surface of the recess, and to form a vent slit between a side wall of the recess and a side edge surface of the second substrate;
    a plurality of electrodes attached to the first or second substrate in the reaction chamber; and
    a reaction reagent located in the reaction chamber and causing the biochemical reaction with the sample.

12. The apparatus according to claim 11, wherein the width of the second substrate is smaller than the width of the recess.

13. A method of manufacturing an apparatus for measuring a biomaterial, comprising:
    manufacturing a first substrate having a recess formed in an upper surface thereof;
    manufacturing a second substrate having a plurality of reaction electrodes in which a biochemical reaction of a sample occurs and a plurality of delivery electrodes transmitting a signal generated by the biochemical reaction to a detector;
    immobilizing a reaction reagent causing the biochemical reaction with the sample to the first or second substrate so as to be located in the recess; and
    attaching the second substrate to the first substrate in the recess such that a reaction chamber is formed between a lower surface of the second substrate and a bottom surface of the recess, the reaction electrodes are directed toward the bottom surface of the recess in the reaction chamber, and a vent slit is formed between a side wall of the recess and a side edge surface of the second substrate, thereby forming a sample inlet.

14. The method according to claim 13, wherein the first substrate is manufactured by injection molding, extrusion molding, or plastic laminating.

* * * * *

UNITED STATES PATENT AND TRADEMARK OFFICE
CERTIFICATE OF CORRECTION

PATENT NO. : 8,753,493 B2
APPLICATION NO. : 13/375276
DATED : June 17, 2014
INVENTOR(S) : Jin-Woo Lee et al.

It is certified that error appears in the above-identified patent and that said Letters Patent is hereby corrected as shown below:

In the Claims:

- Claim 4, line 2, the word "folined" should read -- formed --.

- Claim 4, line 3, the word "one" should be removed.

Signed and Sealed this
Seventh Day of October, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,753,493 B2  Page 1 of 1
APPLICATION NO. : 13/375276
DATED : June 17, 2014
INVENTOR(S) : Jin-Woo Lee et al.

It is certified that error appears in the above-identified patent and that said Letters Patent is hereby corrected as shown below:

In the Claims:

- Col. 9, line 38, Claim 4, the word "folined" should read -- formed --.

- Col. 9, line 39, Claim 4, the word "one" should be removed.

This certificate supersedes the Certificate of Correction issued October 7, 2014.

Signed and Sealed this
Eleventh Day of November, 2014

Michelle K. Lee
*Deputy Director of the United States Patent and Trademark Office*